(12) United States Patent
Kinugasa

(10) Patent No.: US 9,188,552 B2
(45) Date of Patent: Nov. 17, 2015

(54) X-RAY SPECTROMETER AND SAMPLE ANALYZER

(71) Applicant: JEOL Ltd., Tokyo (JP)

(72) Inventor: Genki Kinugasa, Tokyo (JP)

(73) Assignee: JEOL Ltd., Tokyo (JP)

(*) Notice: Subject to any disclaimer, the term of this patent is extended or adjusted under 35 U.S.C. 154(b) by 62 days.

(21) Appl. No.: 14/225,718

(22) Filed: Mar. 26, 2014

(65) Prior Publication Data

US 2015/0276630 A1 Oct. 1, 2015

(51) Int. Cl.
| | |
|---|---|
| *G01N 23/223* | (2006.01) |
| *G01N 23/207* | (2006.01) |
| *G01T 1/24* | (2006.01) |
| *G01T 1/17* | (2006.01) |

(52) U.S. Cl.
CPC .......... *G01N 23/2076* (2013.01); *G01N 23/223* (2013.01); *G01T 1/17* (2013.01); *G01T 1/247* (2013.01)

(58) Field of Classification Search
CPC .......... G01N 23/223; G01N 2223/076; G01N 23/2206; G01N 23/207; G01N 23/2076; G01N 2223/6113
See application file for complete search history.

(56) References Cited

U.S. PATENT DOCUMENTS

| | | | |
|---|---|---|---|
| 5,774,522 A * | 6/1998 | Warburton | 378/91 |
| 2011/0042561 A1* | 2/2011 | Miller et al. | 250/282 |

FOREIGN PATENT DOCUMENTS

JP 2007327902 A 12/2007

* cited by examiner

*Primary Examiner* — Hoon Song
(74) *Attorney, Agent, or Firm* — The Webb Law Firm

(57) ABSTRACT

An X-ray spectrometer (100) capable of reducing the effects of noises includes: an X-ray detector (110) outputting a staircase waveform (S110); a first differential filter (120) converting the staircase waveform (S110) into a first pulsed signal (S120); an event detection portion (140) detecting whether the first pulsed signal (S120) has exceeded a threshold value; a noise event detection portion (150) determining whether the first pulsed signal (S120) in excess of the threshold value is shorter than a given time; a second differential filter (160) converting the staircase waveform (S110) into a second pulsed signal (S160) having peaks whose heights correspond to the heights of the steps of the staircase waveform; a maximum value detection portion (170) detecting pulsed signal (S160) if the first pulsed signal (S120) exceeds a threshold value; and a decision portion (180) making a decision based on the noise event detection portion (150).

4 Claims, 12 Drawing Sheets

X-RAY SPECTROMETER AND SAMPLE ANALYZER

BACKGROUND OF THE INVENTION

1. Field of the Invention

The present invention relates to an X-ray spectrometer and also to a sample analyzer.

2. Description of Related Art

Known X-ray spectrometers include energy-dispersive X-ray spectrometers (EDS) and wavelength-dispersive X-ray spectrometers (WDS).

In an energy-dispersive X-ray spectrometer, X-rays produced from a sample are directly detected by a semiconductor detector and converted into an electrical signal for spectroscopic analysis.

For example, in an X-ray fluorescence (XRF) analyzer equipped with an energy-dispersive X-ray detector and disclosed in JP-A-2007-327902, X-rays are first detected by a semiconductor detector. The output from the semiconductor detector is amplified by a preamplifier and a pulsed voltage signal of staircase waveform is produced. The pulsed voltage signal is shaped into pulses having pulse heights corresponding to the heights of the steps of the staircase waveform. The pulses are digitized by an A/D converter and discriminated by a multichannel analyzer according to their pulse heights. The numbers of pulses in different pulse height ranges are counted, and a graph of a distribution of pulse heights (energy spectrum/histogram) is created.

FIG. 9 is a functional block diagram of a related art X-ray spectrometer 1, showing its configuration.

In the X-ray spectrometer 1, the output signal from an X-ray detector 10 is analyzed by signal processing circuitry 2 by a pulse-height technique. The result of the analysis is obtained by a personal computer (PC) 50 and displayed as a spectrum.

Processing performed by the signal processing circuitry 2 is now described by referring to FIGS. 10A-10B, 11A-11C, and 12. FIGS. 10A and 10B depict the processing performed by a main filter 20. FIGS. 11A-11C depict the processing performed by an event detection and processing portion 30. FIG. 12 depicts the processing performed by a pulse height analysis and processing portion 40.

The main filter 20 converts the output of a staircase waveform S10 from the X-ray detector 10 shown in FIG. 10A into a pulsed signal S20 shown in FIG. 10B, where the vertical axis indicates X-ray energy level.

The event detection and processing portion 30 converts the output of staircase waveform S10 from the X-ray detector 10 shown in FIG. 10A into a pulsed signal S3 as shown FIG. 11B, where the vertical axis indicates X-ray energy level. The event detection and processing portion 30 sets a threshold value TH for the pulsed signal S3. As shown FIGS. 11B and 11C, when the pulsed signal S3 exceeds the threshold value TH, the event detection and processing portion 30 outputs an event signal S30.

The pulse height analysis and processing portion 40 analyzes the peak heights of the pulsed signal S20, based on the output signal S20 from the main filter 20 and on the event signal S30 from the event detection and processing portion 30. As shown in FIG. 12, the pulse height analysis and processing portion 40 starts an operation for detecting a maximum value of the pulsed signal S20 in response to the event signal S30. Then, the pulse height analysis and processing portion 40 detects a maximum value of the pulsed signal S20 within a period L corresponding to the time constant of the main filter 20. The result is sent as an X-ray energy signal S40 to the personal computer 50.

The personal computer 50 discriminates the pulses of the X-ray energy signal S40 according to X-ray energy level, counts the numbers of the pulses in the individual energy levels, and converts them into an X-ray spectrum in which the vertical axis indicates the number of counts and the horizontal axis indicates X-ray energy level.

In the X-ray spectrometer 1, the event detection and processing portion 30 regards every X-ray photon exceeding the threshold value TH as an X-ray event and produces the event signal S30. However, as shown in FIG. 13, the pulsed signal S3 may involve noise. This noise may exceed the threshold value TH.

Since the event exceeding the threshold value TH is a noise, this event has an energy level of 0. In spite of an event with 0 energy level, the event signal S30 is output. Therefore, the pulse height analysis and processing portion 40 performs an operation for detecting a maximum value. Accordingly, in the personal computer 50, the event is counted as if having a low energy level rather than energy level 0. As a result, the background intensity on the lower energy side of the X-ray spectrum may be increased or the X-ray spectrum may be observed to have a peak corresponding to an element not present in the sample.

FIG. 14 is an X-ray spectrum generated when B (boron) is measured by the related art X-ray spectrometer 1.

As shown in FIG. 14, a peak is observed on the lower energy side of the X-ray spectrum in spite of the fact that no element is present in practice.

SUMMARY OF THE INVENTION

In view of the foregoing problem, the present invention has been made. According to some aspects of the present invention, it is possible to offer X-ray spectrometer and sample analyzer capable of reducing the effects of noises.

(1) An X-ray spectrometer associated with the present invention includes: an X-ray detector for detecting X-rays and outputting a staircase waveform having steps whose heights correspond to energy levels of the X-rays; a first differential filter having a time constant and operative to convert the staircase waveform into a first pulsed signal having peaks whose heights correspond to the heights of the steps; an event detection portion for making a decision as to whether the first pulsed signal has exceeded a threshold value; a noise event detection portion for making a decision as to whether a period during which the first pulsed signal is in excess of the threshold value is shorter than a given time; a second differential filter having a time constant longer than the time constant of the first differential filter and operative to convert the staircase waveform into a second pulsed signal having peaks whose heights correspond to the heights of the steps; a maximum value detection portion which, if the first pulsed signal is judged to be in excess of the threshold value, starts to detect a maximum value of the second pulsed signal; and a decision portion for making a decision as to whether information about the maximum value is output, based on the decision made by the noise event detection portion.

In this X-ray spectrometer, when the first pulsed signal exceeds the threshold value, it is possible to make a decision as to whether peaks exceeding the threshold value are attributed to noise. Therefore, if the decision is that the peaks exceeding the threshold value arise from noise, it is possible to refrain from outputting information about the peaks. Accordingly, peaks caused by noises are not reflected in the X-ray spectrum. Consequently, the effects of peaks caused by noises can be reduced. Hence, it is possible to prevent increases in the background intensity on the lower energy side of the X-ray spectrum and observation of artifact peaks in the X-ray spectrum which correspond to elements not contained in the sample in practice.

(2) Another X-ray spectrometer associated with the present invention includes: an X-ray detector for detecting X-rays and outputting a staircase waveform having steps whose heights correspond to energy levels of the X-rays; a first differential filter having a time constant and operative to convert the staircase waveform into a first pulsed signal having peaks whose heights correspond to the heights of the steps; an event detection portion for making a decision as to whether the first pulsed signal has exceeded a first threshold value; a noise event detection portion for making a decision as to whether the first pulsed signal is below a second threshold value; a second differential filter having a time constant longer than the time constant of the first differential filter and operative to convert the staircase waveform into a second pulsed signal having peaks whose heights correspond to the heights of the steps; a maximum value detection portion which, if the first pulsed signal is judged to be in excess of the first threshold value, starts to detect a maximum value of the second pulsed signal; and a decision portion for making a decision as to whether information about the maximum value is output, based on the decision made by the noise event detection portion.

In this X-ray spectrometer, when the first pulsed signal exceeds the first threshold value, it is possible to make a decision as to whether peaks exceeding the first threshold value are attributed to noise. Therefore, if the decision is that the peaks exceeding the first threshold value are induced by noise, it is possible to refrain from outputting information about the peaks. Accordingly, in the X-ray spectrum, the peaks induced by noise are not reflected. The effects of the peaks induced by noise can be reduced. Hence, it is possible to prevent increases in the background intensity on the lower energy side of the X-ray spectrum and observation of peaks in the X-ray spectrum which correspond to elements not contained in the sample in practice.

(3) In one feature of this X-ray spectrometer, the peaks of the first pulsed signal may appear on a positive side of a reference level. The first threshold value may set on the positive side. The second threshold value may be set on a negative side of the reference level.

(4) A sample analyzer associated with the present invention includes an X-ray spectrometer associated with the present invention.

This sample analyzer includes the X-ray spectrometer associated with the present invention and, therefore, the effects of noises can be reduced.

BRIEF DESCRIPTION OF THE DRAWINGS

FIGS. 3A-3G are schematic waveform diagrams of output signals from various components of the X-ray spectrometer shown in FIG. 1.

FIGS. 7A-7H are waveform diagrams of output signals from various components of the X-ray spectrometer shown in FIG. 6.

DESCRIPTION OF THE INVENTION

The preferred embodiments of the present invention are hereinafter described in detail with reference to the drawings. It is to be understood that the embodiments provided below do not unduly restrict the scope and content of the present invention delineated by the appended claims and that not all the configurations described below are essential constituent components of the invention.

1. First Embodiment

1.1. Configuration of X-Ray Spectrometer

Figure 1:
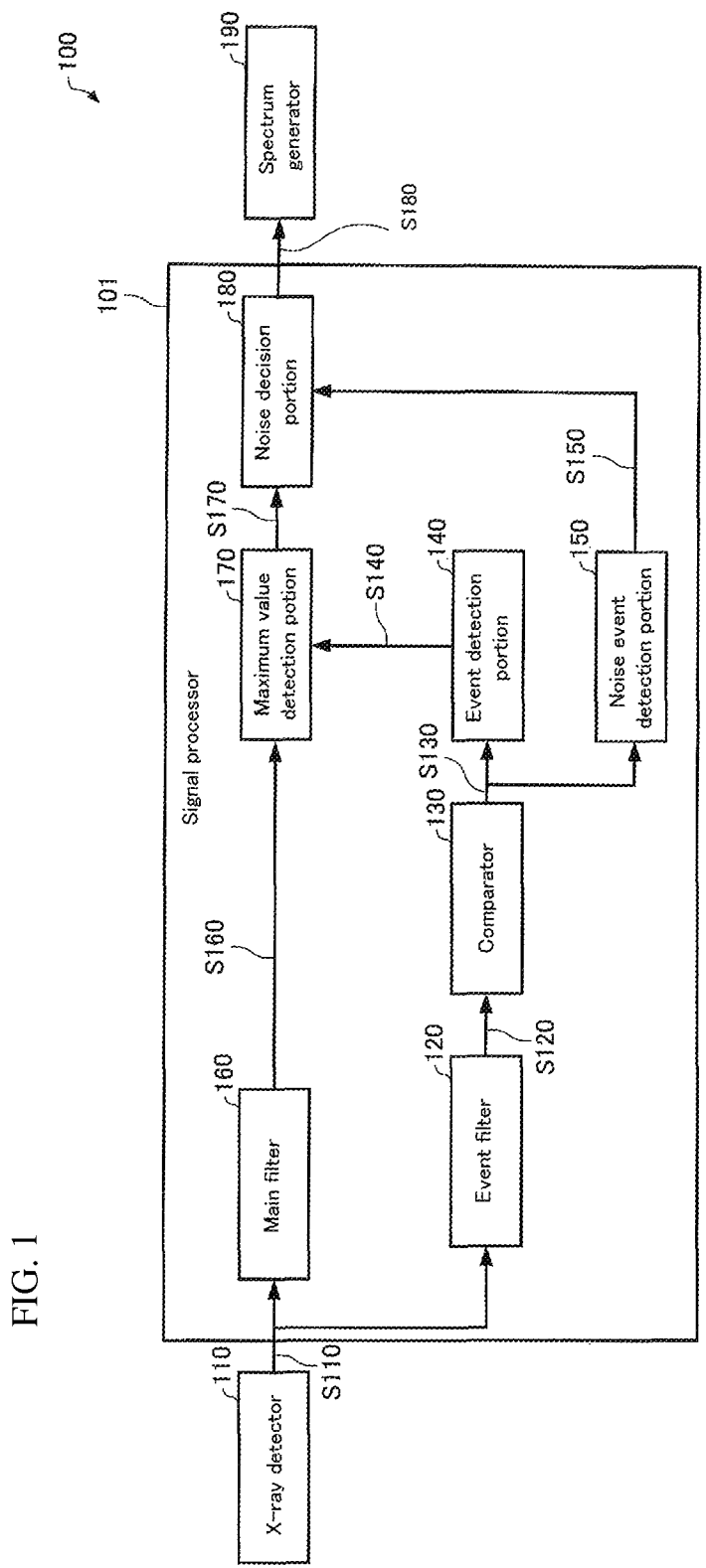
FIG. 1 is a functional block diagram of an X-ray spectrometer associated with a first embodiment of the present invention, showing the configuration of the spectrometer.

First, the configuration of an X-ray spectrometer associated with a first embodiment of the present invention is described by referring to FIG. 1, which is a functional block diagram of the X-ray spectrometer, 100, showing its configuration.

As shown in FIG. 1, the X-ray spectrometer 100 is configured including an X-ray detector 110, a signal processor 101, and a spectrum generator 190.

The X-ray spectrometer 100 is an energy-dispersive X-ray spectrometer.

The X-ray detector 110, which detects X-rays, is a semiconductor detector such as a Si (Li) detector having a single silicon crystal into which lithium has been diffused (known as drifting) or a silicon drift detector having Si to which a drift voltage is applied. The detector 110 is an energy-dispersive detector and may be equipped with an amplifier that amplifies the output from the semiconductor detector and provides the amplified output.

Figure 2:
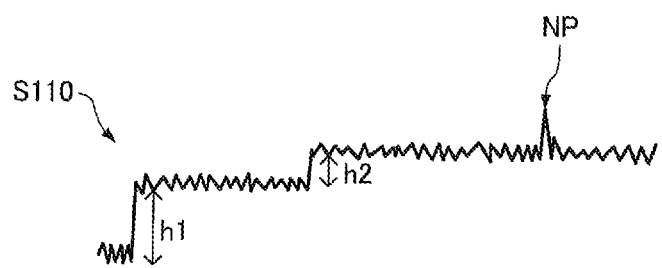
FIG. 2 is a schematic waveform diagram of one example of signal delivered from an X-ray detector included in the X-ray spectrometer shown in FIG. 1.

FIG. 2 is a waveform diagram showing one example of the output signal S110 from the X-ray detector 110. The X-ray detector 110 detects X-rays and outputs a staircase waveform having steps of heights h1 and h2 corresponding to the energy levels of the detected X-rays. That is, the heights h1 and h2 of the steps of the output signal S110 correspond to the energy levels of the detected X-rays. In the example shown in FIG. 2, an X-ray having an energy level corresponding to the height h1 and an X-ray having an energy level corresponding to the height h2 are detected.

The signal processor 101 has an event filter 120 and a main filter 160 to which the output signal S110 of staircase waveform from the X-ray detector 110 is applied.

The signal processor 101 is configured including a comparator 130, an event detection portion 140, a noise event detection portion 150, a maximum value detection portion 170, and a noise decision portion 180, as well as the event filter 120 (referred to also as the first differential filter) and the main filter 160 (referred to also as the second differential filter). The functions of the signal processor 101 can be accomplished, for example, by dedicated hardware circuitry or a personal computer.

The event filter 120 converts the output signal S110 from the X-ray detector 110 into a pulsed signal S120 having peaks whose pulse heights correspond to the heights h1 and h2 of the steps. The event filter 120 functions as a differential filter for differentiating the output signal S110 from the X-ray detector 110. The time constant of the event filter 120 is smaller than that of the main filter 160 described later. A time constant is an index indicating the speed of response. As the time constant is reduced, the response is made faster and vice versa.

Figure 3A:
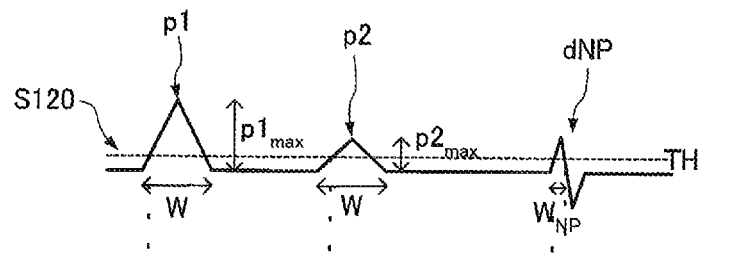

FIG. 3A is a waveform diagram schematically showing one example of the output signal S120 from the event filter 120. The height $p1_{max}$ of one peak p1 of the pulsed output signal S120 shown in FIG. 3A corresponds to the height h1 of one step of the output signal S110 of staircase waveform shown in FIG. 2. The height $p2_{max}$ of another peak p2 of the pulsed output signal S120 shown in FIG. 3A corresponds to the height h2 of another step of the staircase-waveform output signal S110 shown in FIG. 2. That is, the height $p1_{max}$ of the peak p1 and the height $p2_{max}$ of the peak p2 correspond to the energy levels of the X-rays detected by the X-ray detector 110.

A peak dNP shown in FIG. 3A corresponds to a noise peak NP on the output signal S110 of staircase waveform from the X-ray detector 110 shown in FIG. 2. That is, the peak dNP is obtained by differentiating the noise peak NP.

In this way, the peaks p1, p2 having the heights $p1_{max}$ and $p2_{max}$ corresponding to energy levels of X-rays and the noise-induced peak dNP appear in the pulsed output signal S120 from the event filter 120 shown in FIG. 3A.

The pulsed output signal S120 from the event filter 120 is applied to the comparator 130.

The comparator 130 compares the pulsed output signal S120 from the event filter 120 and a reference signal indicative of the threshold value TH.

Figure 3B:
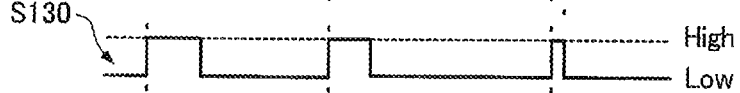

FIG. 3B is a waveform diagram schematically showing one example of the output signal S130 from the comparator 130. As shown in FIG. 3B, when the pulsed output signal S120 from the event filter 120 goes higher than the threshold value TH, the output signal S130 from the comparator 130 goes high. When the signal S120 goes lower than the threshold value TH, the signal S130 goes low. The threshold value TH is set, for example, to such a value that the rising edges of the peaks p1 and p2 can be detected.

The output signal S130 from the comparator 130 is applied to the event detection portion 140 and to the noise event detection portion 150.

The event detection portion 140 makes a decision as to whether the pulsed output signal S120 from the event filter 120 exceeds the threshold value TH. In particular, when the pulsed output signal S120 from the event filter 120 exceeds the threshold value TH, the event detection portion 140 outputs an event signal S140.

Figure 3C:
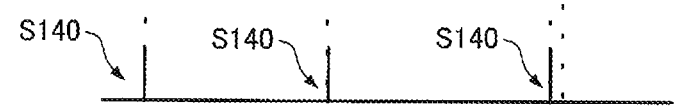

FIG. 3C is a waveform diagram schematically showing one example of the output signal S140 (i.e., event signal) from the event detection portion 140. When the output signal S130 from the comparator 130 is switched from Low level to High level as shown in FIG. 3C, the event detection portion 140 outputs the event signal S140. In this way, the event detection portion 140 can sense that the pulsed output signal S120 from the event filter 120 has exceeded the threshold value TH, i.e., the rising edges of the peaks p1, p2, and dNP of the pulsed output signal S120.

The output signal (event signal) S140 from the event detection portion 140 is applied to the maximum value detection portion 170.

The noise event detection portion 150 makes a decision as to whether the time for which the pulsed output signal S120 from the event filter 120 is in excess of the threshold value TH is shorter than a given time. If the decision is affirmative (Yes), the noise event detection portion 150 outputs a noise event signal S150.

Figure 3D:

FIG. 3D is a waveform diagram schematically showing one example of the output signal S150 from the noise event detection portion 150. The noise event detection portion 150 measures the time for which the output signal S130 (see FIG. 3B) from the comparator 130 is kept at High level, i.e., from the instant when the output signal S130 from the comparator 130 is switched from Low to High level to the instant when the signal returns to Low level. If the decision is that the time for which the output signal S130 from the comparator 130 is kept at High level is shorter than the given time as shown in FIG. 3D, the noise event detection portion 150 outputs the noise event signal S150.

The widths W (see FIG. 3A) of the peaks p1 and p2 of the pulsed output signal S120 from the event filter 120 are determined by the time constant of the event filter 120. Accordingly, the widths W of the peaks p1 and p2 of the pulsed output signal S120 from the event filter 120 are almost equal irrespective of the heights h1 and h2 of the steps of the output signal S110 (i.e., regardless of X-ray energy level) of staircase waveform from the X-ray detector 110 shown in FIG. 2.

On the other hand, the peak dNP of the pulsed output signal from the event filter 120 is not a step of the staircase waveform S110 but a peak produced by differentiating the noise peak NP (see FIG. 2) appearing on the staircase waveform S110. Therefore, the width $W_{NP}$ of the peak dNP of the pulsed output signal S120 from the event filter 120 is narrower than the widths W of the peaks p1 and p2.

Accordingly, the noise event detection portion 150 can make a decision as to whether any peak on the pulsed output signal S120 which exceeds the threshold value TH is the peak dNP attributed to the noise peak NP, by making a decision as to whether the time for which the pulsed output signal S120 is in excess of the threshold value TH is shorter than the given time.

For example, when the time for which the pulsed output signal S120 is in excess of the threshold value TH is shorter than the widths W of the peaks p1 and p2 having the heights $p1_{max}$ and $p2_{max}$, respectively, corresponding to the energy levels of the X-rays, the noise event detection portion 150 can determine that the peak dNP is attributed to the noise peak NP.

In the noise event detection portion 150, no restriction is placed on the given time providing a basis on which to make a decision as to whether the peak is attributed to noise, as long as it is possible to discriminate the peaks p1, p2 attributed to energy levels of X-rays from the peak dNP attributed to the noise peak NP on the pulsed output signal S120 from the event filter 120.

The output signal (noise event signal) S150 from the noise event detection portion 150 is applied to the noise decision portion 180.

The main filter 160 converts the output signal S110 of staircase waveform from the X-ray detector 110 into a second pulsed signal S160 having peaks of heights corresponding to the heights of the steps. The main filter 160 functions as a differential filter for differentiating the output signal S110 from the X-ray detector 110. The time constant of the main filter 160 is longer than that of the event filter 120.

Figure 3E:
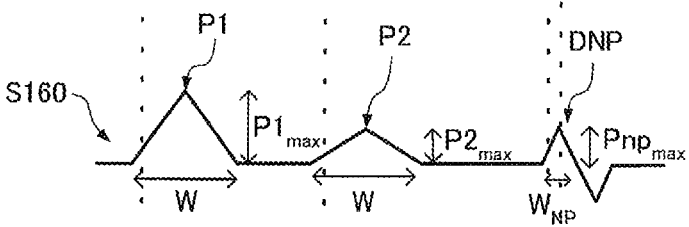

FIG. 3E is a waveform diagram schematically showing one example of the output signal S160 from the main filter 160. The height $P1_{max}$ of a peak P1 of the pulsed output signal S160 shown in FIG. 3E corresponds to the height h1 of the step of the output signal S110 of staircase waveform shown in FIG. 2. The height $P2_{max}$ of another peak P2 of the pulsed output signal S160 shown in FIG. 3E corresponds to the height h2 of the step of the output signal S110 of staircase waveform shown in FIG. 2. A peak DNP of the pulsed output signal S160 shown in FIG. 3E corresponds to the noise peak NP of the output signal S110 of staircase waveform shown in FIG. 2.

The pulsed output signal S160 from the main filter 160 is applied to the maximum value detection portion 170.

The maximum value detection portion 170 detects a maximum value of peaks of the pulsed output signal S160 from the main filter 160. If the event detection portion 140 has determined that the output signal S120 from the event filter 120 has exceeded the threshold value TH, the maximum value detection portion 170 starts detection of a maximum value of the pulsed output signal S160.

FIG. 3F is a waveform diagram illustrating processing performed by the maximum value detection portion 170. As shown in FIG. 3F, when the event signal S140 is entered, the maximum value detection portion 170 starts detection of a maximum value of the pulsed output signal S160. The maximum value detection portion 170 performs processing for detecting a maximum value of the pulsed output signal S160 within a given period L since the initiation of the detection. For example, the given period L is from the instant when one peak (such as peak P1) of the output signal S160 rises to the instant when this peak falls. The given period L has been preset, for example, according to the time constant of the main filter 160. When the given period L passes, the maximum value detection portion 170 outputs information about the detected maximum value of the pulsed output signal S160.

The output signal S170 from the maximum value detection portion 170 is applied to the noise decision portion 180.

Based on the decision made by the noise event detection portion 150, the noise decision portion 180 makes a decision as to whether information about the maximum value of the pulsed output signal S160 detected by the maximum value detection portion 170 is delivered.

Figure 3G:
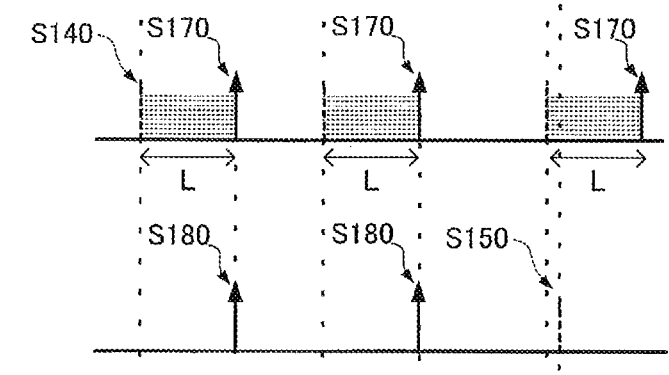

FIG. 3G is a waveform diagram illustrating processing performed by the noise decision portion 180. When the noise event signal S150 is not input during the given period L as shown in FIG. 3G, the noise decision portion 180 outputs information about maximum values $P1_{max}$ and $P2_{max}$ of the pulsed output signal S160. When the noise event signal S150 is entered within the given period L, the noise decision portion 180 performs processing for refraining from outputting the information about the maximum value $Pnp_{max}$ of the pulsed output signal S160. This can prevent the noise peak NP (see FIG. 2) from being reflected in the X-ray spectrum generated by the spectrum generator 190.

The output signal S180 from the noise decision portion 180 is applied to the spectrum generator 190.

On receiving the output signal S180 from the noise decision portion 180, the spectrum generator 190 discriminates pulses according to the maximum values $P1_{max}$ and $P2_{max}$, counts the pulses in terms of their energy levels, and generates an X-ray spectrum (also referred to as an energy spectrum or a graph of a distribution of pulse heights) in which the horizontal axis indicates the maximum values (heights) $P1_{max}$ and $P2_{max}$ of the peaks P1 and P2 of the pulsed output signal S160, i.e., X-ray energy levels, and the vertical axis indicates the number of counts.

Figure 4:
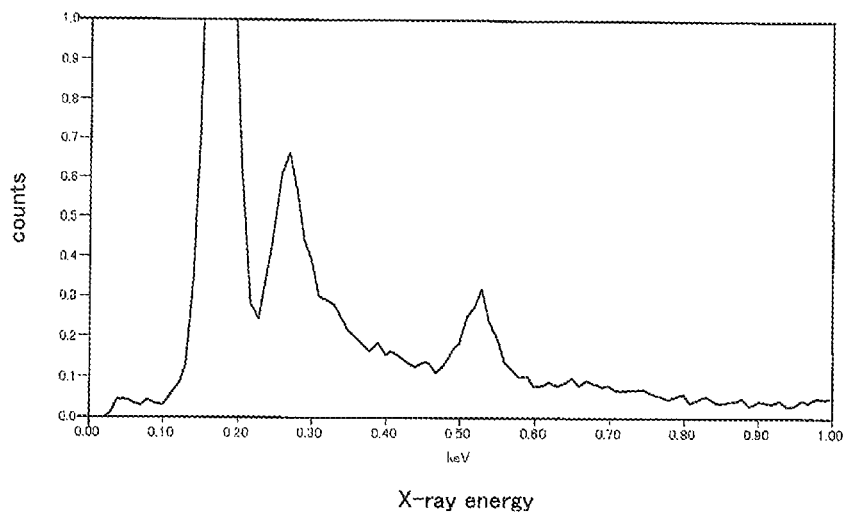
FIG. 4 is a graph showing one example of X-ray spectrum generated by a spectrum generator included in the X-ray spectrometer shown in FIG. 1.

FIG. 4 is a graph schematically showing one example of X-ray spectrum generated by the spectrum generator 190.

The functions of the spectrum generator 190 can be accomplished, for example, by a personal computer (PC) or dedicated hardware circuitry.

1.2. Operation of X-Ray Spectrometer

The operation of the X-ray spectrometer 100 is next described.

When the X-ray detector 110 detects X-rays, the detector outputs the output signal S110 of staircase waveform shown in FIG. 2. The event filter 120 converts the output signal S110 of staircase waveform from the X-ray detector 110 into the pulsed signal S120 (see FIG. 3A). The pulsed output signal S120 from the event filter 120 is applied to the comparator 130. The main filter 160 converts the output signal S110 of staircase waveform from the X-ray detector 110 into the pulsed signal S160 in the same way as the event filter 120. The pulsed output signal S160 from the main filter 160 is applied to the maximum value detection portion 170.

When the pulsed signal S120 exceeds the threshold value TH at an instant t1 because of the presence of the peak p1, the output signal S130 from the comparator 130 is switched from Low to High level. Consequently, the event detection portion 140 outputs the event signal S140. On receiving the event signal S140, the maximum value detection portion 170 starts to detect a maximum value of the pulsed output signal S160. The maximum value detection portion 170 detects the maximum value $P1_{max}$ of the pulsed output signal S160 during the given period L.

When the output signal S130 from the comparator 130 is switched from Low to High level at the instant t1, the noise event detection portion 150 measures the time for which the output signal S130 is kept at High level. Since the peak p1 corresponds to an X-ray energy level, the time for which the signal is kept at High level is the given time or longer. Accordingly, the noise event detection portion 150 determines that the time for which the output signal S130 from the comparator 130 is kept at High level is not shorter than the given time and does not output the noise event signal S150.

At an instant t2 that is the given period L later than the instant t1, the maximum value detection portion 170 outputs the output signal S170 including information about the maximum value $P1_{max}$. During the given period L beginning with the instant t1, the noise event signal S150 is not entered to the noise decision portion 180. Therefore, the noise decision portion 180 outputs the output signal S180 including information about the maximum value $P1_{max}$. The spectrum generator 190 counts the X-ray energy (pulse height) corresponding to the maximum value $P1_{max}$ according to energy level in response to the output signal S180.

If the pulsed signal S120 again exceeds the threshold value TH at an instant t3 because of its peak p2, the same processing is performed as for the aforementioned peak p1. At an instant t4 that is the given period L later than the instant t3, the maximum value detection portion 170 outputs the output signal S170 including information about the maximum value $P2_{max}$. The output signal S170 is applied to the noise decision portion 180.

The peak p2 corresponds to an X-ray energy level in the same way as the peak p1 and, therefore, is maintained at High level for the given time or longer. Therefore, the noise event detection portion 150 determines that the time for which the output signal S130 from the comparator 130 is kept at High level is not shorter than the given time and does not output the noise event signal S150. Consequently, the noise event signal S150 is not entered to the noise decision portion 180 during the given period L beginning with the instant t3. The noise decision portion 180 outputs the output signal S180 including the information about the maximum value $P2_{max}$. The spectrum generator 190 counts the X-ray (pulse height) corresponding to the maximum value $P2_{max}$ according to energy level in response to the output signal S180.

Then, when the pulsed signal S120 exceeds the threshold value TH at an instant t5 because of the peak dNP, the same processing is performed as for the above-described peaks p1 and p2. After a lapse of the given period L from the instant t5, the maximum value detection portion 170 provides the output signal S170 including information about the maximum value $Pnp_{max}$. The output signal S170 is applied to the noise decision portion 180.

The peak dNP corresponds to the noise peak NP (see FIG. 2) and so the peak dNP is kept at High level for a time shorter than the given time. Accordingly, the noise event decision portion 150 determines that the time for which the output signal S130 from the comparator 130 is kept at High level is shorter than the given time and outputs the noise event signal S150 at an instant t6 that is later than the instant t5 by a period shorter than the given period L.

Consequently, the noise event signal S150 is applied to the noise decision portion 180 before the given period L passes since the instant t5. The noise decision portion 180 does not deliver an output signal including information about the maximum value $Pnp_{max}$. Therefore, the spectrum generator 190 does not count the X-ray (pulse height) corresponding to the maximum value $Pnp_{max}$ according to energy level.

An X-spectrum can be created by repeating the above-described processing steps.

In the X-ray spectrometer 100 associated with the present embodiment, the noise event detection portion 150 makes a decision as to whether the pulsed signal S120 from the event filter 120 has exceeded the threshold value TH. Since the noise decision portion 180 makes a decision as to whether information about the maximum value of the pulsed output signal S160 from the main filter 160 is delivered, based on the decision made by the noise event detection portion 150. Therefore, when the pulsed signal S120 exceeds the threshold value TH, it is possible to judge whether peaks exceeding the threshold value TH are attributed to noise. Thus, if the peaks exceeding the threshold value TH are judged to be attributed to noise, information about these peaks can be prevented from being output. Accordingly, the peaks attributed to noise are not reflected in the X-ray spectrum. The effects of the noise peak NP (see FIG. 2) can be reduced. In consequence, it is possible to prevent increases in the background intensity on the lower energy side of the X-ray spectrum and observation of noise-induced peaks corresponding to peaks not contained in the sample in practice.

Figure 5:
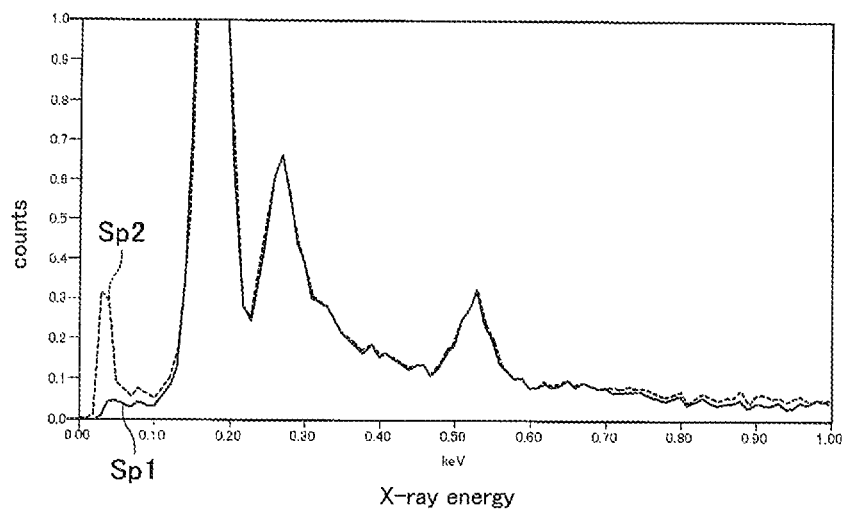
FIG. 5 is a graph providing a comparison of the X-ray spectrum generated by the X-ray spectrometer as shown in FIG. 4 with an X-ray spectrum generated by a related art X-ray spectrometer.
Figure 9:
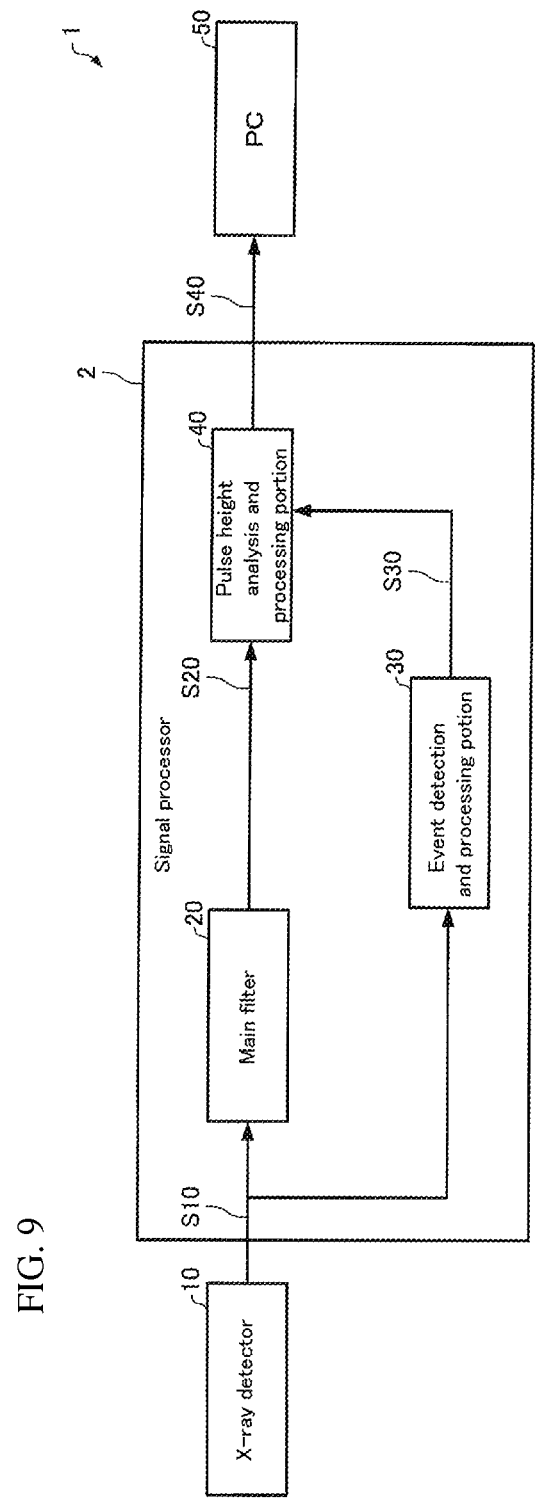
FIG. 9 is a functional block diagram of the related art X-ray spectrometer.
Figure 10A:
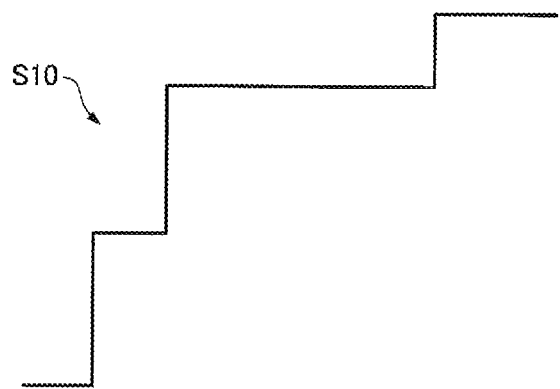
FIGS. 10A-10B are waveform diagrams illustrating processing performed by a main filter included in the related art X-ray spectrometer shown in FIG. 9.
Figure 10B:
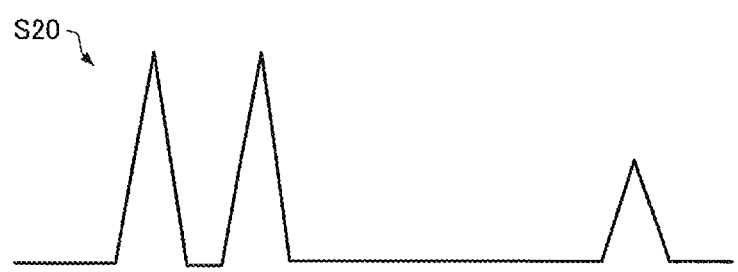
Figure 11A:
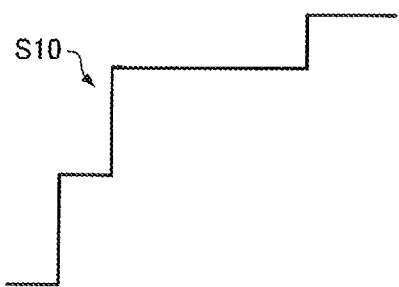
FIGS. 11A-11C are waveform diagrams illustrating processing performed by an event detection and processing portion of the related art X-ray spectrometer shown in FIG. 9.
Figure 11B:
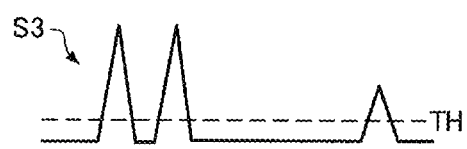
Figure 11C:
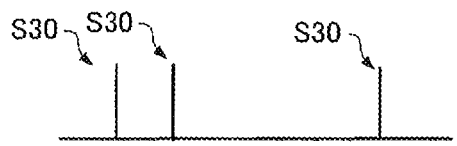
Figure 12:
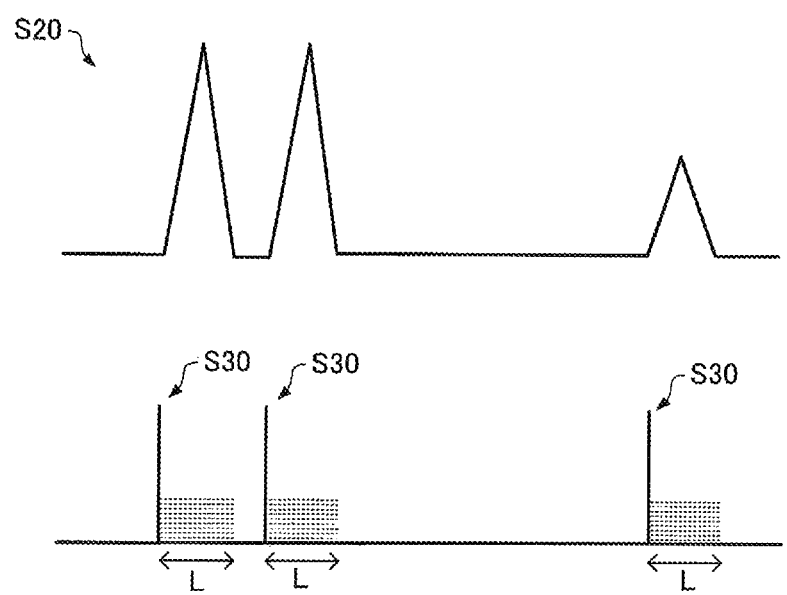
FIG. 12 is a waveform diagram illustrating processing performed by a pulse height analysis and processing portion of the related art X-ray spectrometer shown in FIG. 9.
Figure 13:
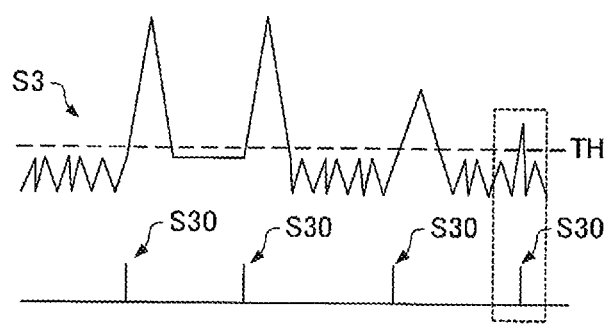
FIG. 13 is a waveform diagram illustrating noise on a pulsed signal from the event detection and processing portion of the related art X-ray spectrometer.
Figure 14:
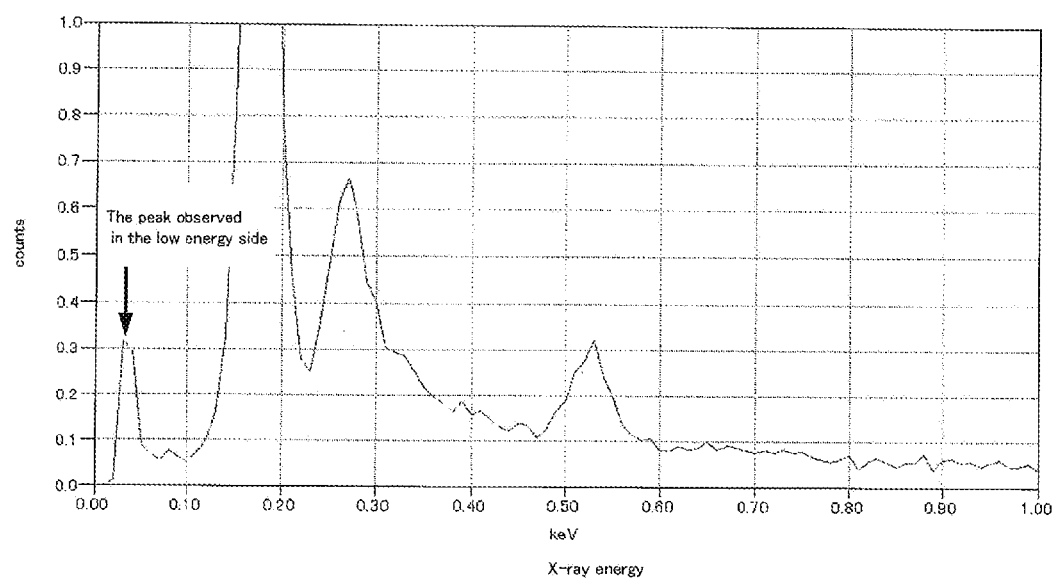
FIG. 14 is an X-ray spectrum obtained when B (boron) is measured by the related art X-ray spectrometer.

FIG. 5 is a graph providing a comparison of an X-ray spectrum obtained by an operation of the X-ray spectrometer 100 associated with the present embodiment with an X-ray spectrum obtained by an operation of the related art X-ray spectrometer 1 (see FIG. 9). In FIG. 5, an X-ray spectrum Sp1 indicated by a solid line has been generated by an operation of the X-ray spectrometer 100, while an X-ray spectrum Sp2 indicated by a dotted line has been generated by an operation of the related art X-ray spectrometer 1. The results have been obtained by making measurements on B (boron).

As shown in FIG. 5, a peak attributed to noise is observed on the lower energy side (0.10 keV or less) of the X-ray spectrum Sp2 generated by the related art X-ray spectrometer 1. In contrast, in the X-ray spectrum Sp1 generated by the X-ray spectrometer 100, this peak is not observed.

2. Second Embodiment 2.1. Configuration of X-Ray Spectrometer

Figure 6:
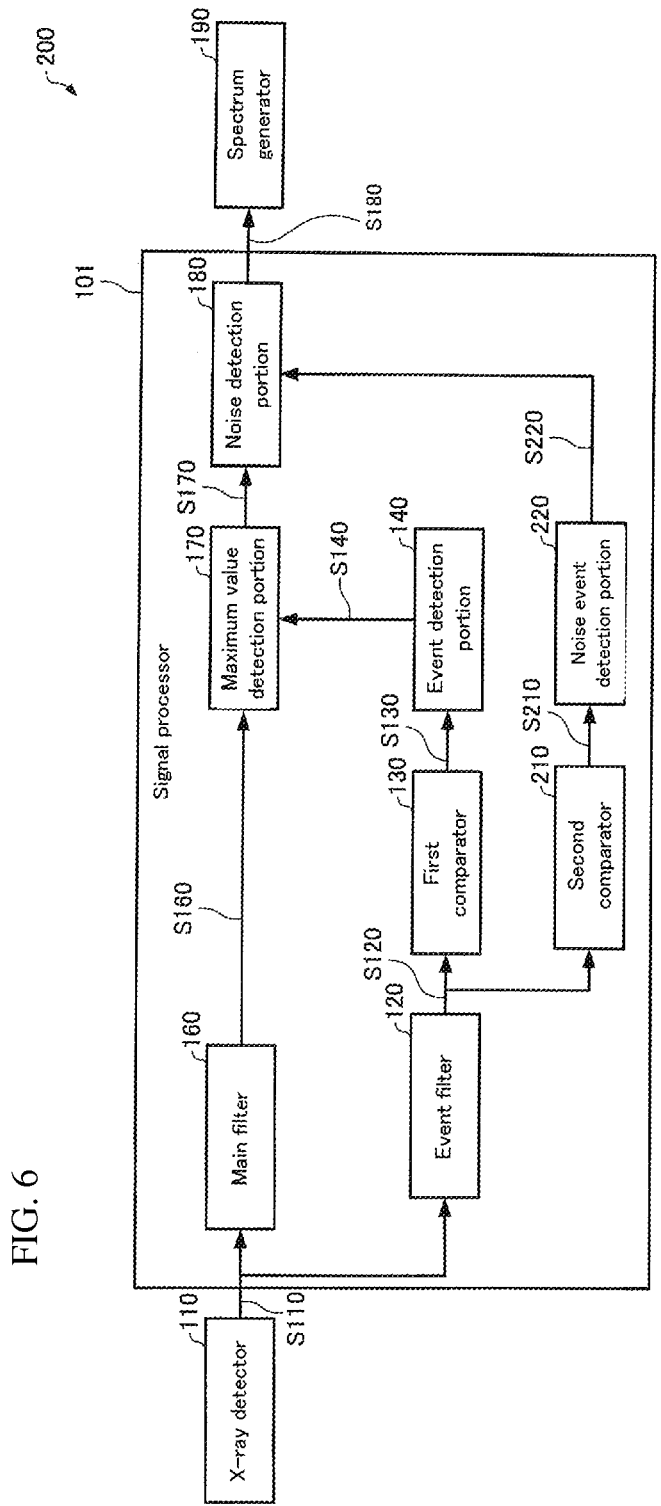
FIG. 6 is a functional block diagram of an X-ray spectrometer associated with a second embodiment of the present invention, showing the configuration of the spectrometer.

The configuration of an X-ray spectrometer associated with a second embodiment of the present invention is next described by referring to the functional block diagram of FIG. 6, where the spectrometer is indicated by reference numeral 200. Those components of the X-ray spectrometer 200 described below which are similar in function to their respective counterparts of the X-ray spectrometer 100 (FIG. 1) associated with the first embodiment are indicated by the same reference numerals as in FIG. 1 and a detailed description thereof is omitted.

In the above-described X-ray spectrometer 100, the noise event detection portion 150 makes a decision as to whether the peak NP is attributed to noise by making a decision as to whether the time for which the pulsed output signal S120 from the event filter 120 is in excess of the threshold value TH is shorter than the given time.

In contrast, in the X-ray spectrometer 200, a noise event detection portion 220 makes a decision as to whether the peak NP is attributed to noise by making a decision as to whether the pulsed output signal S120 from the event filter 120 is below the second threshold value.

The signal processor 101 of the X-ray spectrometer 200 is configured including an event filter 120, a first comparator 130, a second comparator 210, an event detection portion 140, a main filter 160, a maximum value detection portion 170, and a noise decision portion 180, as well as the noise event detection portion 220.

Figure 7A:
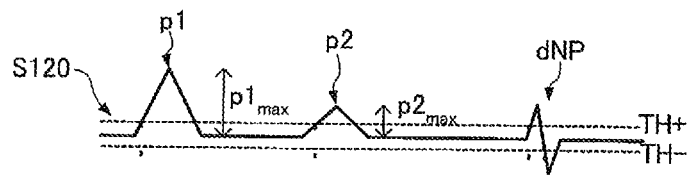

In the X-ray spectrometer 200, as shown in FIG. 6, the pulsed output signal S120 from the event filter 120 is applied to the first comparator 130 and to the second comparator 210. FIG. 7A is a waveform diagram schematically showing one example of the output signal S120 from the event filter 120.

Figure 7B:
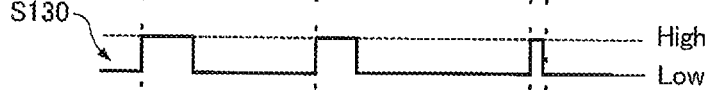
Figure 7C:
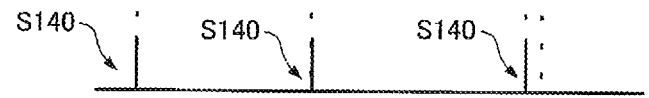

The first comparator 130 compares the pulsed output signal S120 from the event filter 120 and a reference signal indicative of a first threshold value TH+. The first threshold value TH+ can have the same value as the threshold value TH shown in FIG. 3. FIG. 7B is a waveform diagram schematically showing one example of the output signal S130 from the first comparator 130.

The output signal S130 from the first comparator 130 is applied to the event detection portion 140.

The second comparator 210 compares the pulsed output signal S120 from the event filter 120 with a reference signal indicative of a second threshold value TH−.

Figure 7H:
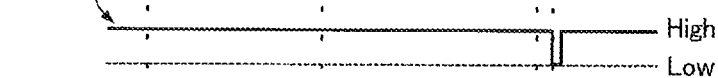

FIG. 7H is a waveform diagram schematically showing one example of the output signal S210 from the second comparator 210. As shown in FIG. 7H, the output signal S210 from the second comparator 210 goes High when the pulsed output signal S120 from the event filter 120 exceeds the second threshold value TH− and goes Low when the signal S120 becomes lower than the second threshold value TH−.

The output signal S210 from the second comparator 210 is applied to the noise event detection portion 220.

The noise event detection portion 220 makes a decision as to whether the pulsed output signal S120 from the event filter 120 has become below the second threshold value TH−. When the pulsed output signal S120 from the event filter 120 has become below the second threshold value TH−, the noise event detection portion 220 outputs a noise event signal S220.

Figure 7D:
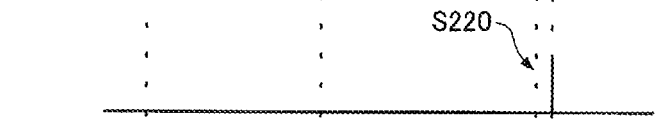
Figure 7E:
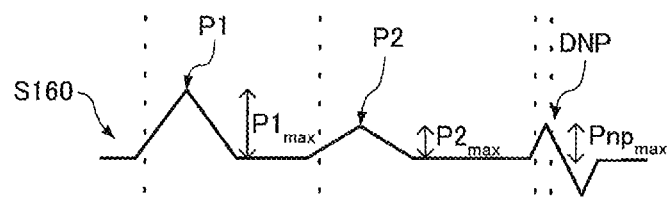
Figure 7G:
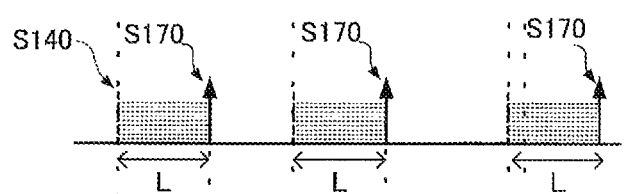

FIG. 7D is a waveform diagram schematically showing one example of the output signal S220 from the noise event detection portion 220. When the output signal S210 from the second comparator 210 is switched from High to Low level as shown in FIG. 7D, the noise event detection portion 220 outputs the noise event signal S220. Consequently, the noise event detection portion 220 can sense that the pulsed output signal S120 from the event filter 120 has become lower than the second threshold value TH−.

The peaks p1 and p2 of the pulsed output signal S120 from the event filter 120 are obtained by passing the steps of the staircase waveform S110 shown in FIG. 2 through a differential filter. Therefore, the peaks p1 and p2 appear on the positive side (described later) as shown in FIG. 7A. Accordingly, the first threshold value TH+ is set on the positive side.

On the other hand, the peak dNP of the pulsed output signal S120 from the event filter 120 is obtained by passing the noise peak NP of the staircase waveform S110 shown in FIG. 2 through a differential filter. Therefore, the peak dNP appears also on the negative side on the opposite side of the positive side where the peaks p1 and p2 appear as shown in FIG. 7A. Consequently, the second threshold value TH− is set on the negative side.

In this way, the noise event detection portion 220 can make a decision as to whether any peak exceeding the first threshold value TH+ for the pulsed output signal S120 is the peak dNP attributed to the noise peak NP (see FIG. 2) by making a decision as to whether the pulsed output signal S120 is below the second threshold value TH− set on the negative side.

The positive side referred to herein is one side of a reference level at which none of the peaks p1, p2, and dNP appear, the reference level being for the pulsed output signal S120 from the event filter 120 shown in FIG. 7A. The negative side is the other side of the reference level.

The noise event signal S220 delivered from the noise event detection portion 220 is applied to the noise decision portion 180.

2.2. Operation of X-Ray Spectrometer

The operation of the X-ray spectrometer 200 is next described.

On detecting X-rays, the X-ray detector 110 outputs the output signal S110 of staircase waveform shown in FIG. 2. The event filter 120 converts the output signal S110 of staircase waveform from the X-ray detector 110 into the pulsed signal S120 (see FIG. 7A). The pulsed output signal S120 from the event filter 120 is applied to the first comparator 130 and to the second comparator 210.

When the pulsed signal S120 exceeds the first threshold value TH+ at the instant t1 because of the presence of the peak p1, the output signal S130 from the first comparator 130 is switched from Low to High level. In response to this, the event detection portion 140 outputs the event signal S140. In response to the event signal S140, the maximum value detection portion 170 starts to detect a maximum value of the output signal S160. The maximum value detection portion 170 detects the maximum value $P1_{max}$ of the pulsed output signal S160 during the given period L.

Within the given period L beginning with the instant t1, the output signal S120 does not become below the second threshold value TH− and so the output signal S210 from the second comparator 210 is kept at High level. Therefore, during the given period T beginning with the instant t1, the noise event detection portion 220 does not output the noise event signal S220.

At the instant t2 that is later than the instant t1 by the given period L, the maximum value detection portion 170 outputs the output signal S170 including information about the maximum value $P1_{max}$. During the given period L beginning with the instant t1, the noise event signal S220 is not applied to the noise decision portion 180. Therefore, the noise decision portion 180 outputs the output signal S180 including information about the maximum value $P1_{max}$. In response to the output signal S180, the spectrum generator 190 counts the X-ray (pulse height) corresponding to the maximum value $P1_{max}$ according to energy level.

When the pulsed signal S120 again exceeds the first threshold value TH+ at the instant t3 because of the presence of the peak p2, the same processing is carried out as for the peak p1. At the instant t4 that is later than the instant t3 by the given period L, the maximum value detection portion 170 outputs the output signal S170 including information about the maximum value $P2_{max}$. The output signal S170 is applied to the noise decision portion 180.

During the given period L beginning with the instant t3, the output signal S120 does not become below the second threshold value TH− and, therefore, the noise event detection portion 220 does not output the noise event signal S220 during the given period L beginning with the instant t3.

At the instant t4 that is later than the instant t3 by the given period L, the maximum value detection portion 170 outputs the output signal S170 including information about the maximum value $P2_{max}$. During the given period L beginning with the instant t3, the noise event signal S220 is not applied to the noise decision portion 180. Therefore, the noise decision portion 180 outputs the output signal S180 including information about the maximum value $P2_{max}$. In response to the output signal S180, the spectrum generator 190 counts the X-ray (pulse height) corresponding to the maximum value $P2_{max}$ according to energy level.

When the pulsed signal S120 exceeds the first threshold value TH+ at the instant t5 because of the presence of the peak dNP, the output signal S130 from the first comparator 130 is switched from Low to High level. In response to this, the event detection portion 140 outputs the event signal S140. In response to this event signal S140, the maximum value detection portion 170 starts to detect a maximum value of the output signal S160. During the given period L, the maximum value detection portion 170 detects the maximum value $Pnp_{max}$ of the pulsed output signal S160.

If the peak dNP swings to the negative side and the pulsed signal S120 becomes lower than the second threshold value TH− at an instant t6, the output signal S210 from the second comparator 210 is switched from High to Low level (see FIG. 7H). Consequently, the noise event detection portion 220 outputs a noise event signal S220 at the instant t6 when the period L does not yet pass since the instant t5.

In consequence, the noise event signal S220 is applied to the noise decision portion 180 before the given period L passes since the instant t5. The noise decision portion 180 does not deliver the output signal including information about the maximum value $Pnp_{max}$. Therefore, the spectrum generator 190 does not count the X-ray (pulse height) corresponding to the maximum value $Pnp_{max}$ according to energy level.

An X-ray spectrum can be generated by repeating the above-described processing steps.

According to the X-ray spectrometer 200 associated with the present embodiment, the noise event detection portion 220 makes a decision as to whether the pulsed signal S120 from the event filter 120 has become lower than the second threshold value TH−. The noise decision portion 180 makes a decision as to whether information about a maximum value of the pulsed output signal S160 from the main filter 160 is output, based on the decision made by the noise event detection portion 150. Therefore, when the pulsed signal S120 exceeds the first threshold value TH+, it is possible to make a decision as to whether the peak exceeding the first threshold value TH+ is attributed to noise. Thus, if the decision is that the peak exceeding the first threshold value TH+ is attributed to noise, it is possible to refrain from outputting information about the peak. Consequently, the peak attributed to noise is not reflected in the X-ray spectrum, and the effects of the noise peak NP (see FIG. 2) can be reduced.

3. Third Embodiment

Figure 8:
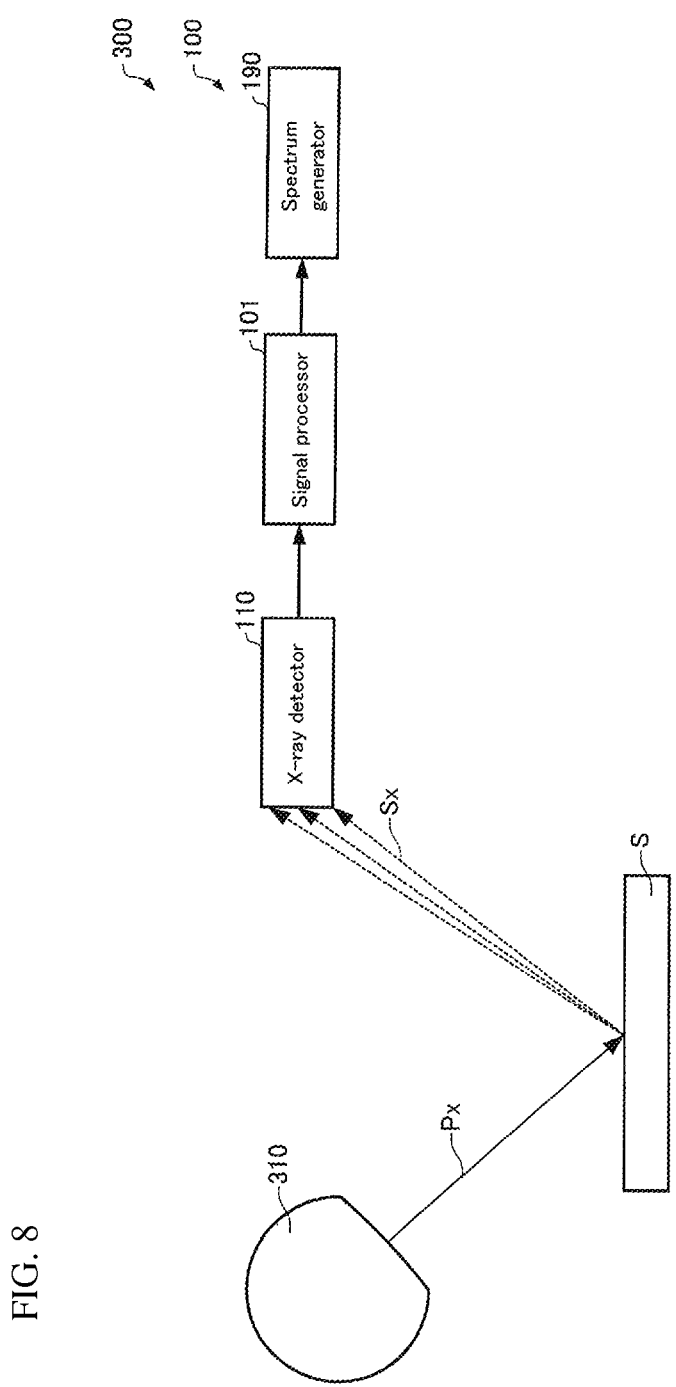
FIG. 8 is a functional block diagram of a sample analyzer associated with a third embodiment of the present invention, showing the configuration of the analyzer.

A sample analyzer associated with a third embodiment of the present invention is next described by referring to the functional block diagram of FIG. 8, where the analyzer is generally indicated by reference numeral 300.

As shown in FIG. 8, the sample analyzer 300 is configured including an X-ray spectrometer associated with the present invention. It is now assumed that the included X-ray spectrometer is the above-described X-ray spectrometer 100.

The sample analyzer 300 is configured including an X-ray irradiation portion 310 and the X-ray spectrometer 100. The sample analyzer 300 irradiates a sample S with primary X-rays, Px, by means of the X-ray irradiation means 310. Secondary X-rays (fluorescent X-rays) Sx emanating from the sample S in response to the irradiation are detected by the X-ray spectrometer 100. The sample analyzer 300 is an energy-dispersive X-ray fluorescence (XRF) analyzer.

The X-ray irradiation portion 310 irradiates the sample S with the primary X-rays, Px. The X-ray irradiation portion 310 is configured, for example, including an X-ray tube and a high voltage source. The X-ray irradiation portion 310 produces the primary X-rays Px, for example, by accelerating thermal electrons generated from a filament by a high voltage and causing the electrons to collide against a metal target in an unillustrated manner.

The primary X-rays Px generated by the X-ray irradiation portion 310 are directed at the sample S. The resulting secondary X-rays (fluorescent X-rays) Sx from the sample S are detected by the X-ray spectrometer 100. The X-ray spectrometer 100 creates an X-ray spectrum based on the detected secondary X-rays Sx.

Since the sample analyzer 300 is configured including the X-ray spectrometer 100, the effects of noise can be reduced.

In the description provided so far, the sample analyzer associated with the present invention is an XRF analyzer which directs X-rays at a sample to emit X-rays from the sample and which detects the generated X-rays. The sample analyzer associated with the present invention may also be an instrument which irradiates a sample with an electron beam or ions to emit X-rays from the sample and which detects the produced X-rays. For example, the sample analyzer associated with the present invention may be an electron microscope (such as a transmission electron microscope (TEM), scanning transmission electron microscope (STEM), or scanning electron microscope (SEM)) equipped with an X-ray spectrometer associated with the present invention or an electron probe microanalyzer.

It is to be noted that the above-described embodiments are merely exemplary and that the present invention is not restricted thereto.

For example, in the X-ray spectrometer 100 shown in FIG. 1, the noise decision portion 180 does not output information about the maximum value $Pnp_{max}$ of the pulsed output signal S160 (see FIG. 3G) if the noise event signal S150 is applied during the given period L. On the other hand, if the noise event signal S150 is applied during the given period L, the noise decision portion 180 may deactivate the maximum value detection portion 170. In this case, information about the maximum value $Pnp_{max}$ of the pulsed output signal S160 is not entered to the noise decision portion 180. It is possible to prevent the noise peak NP (see FIG. 2) from being reflected in the X-ray spectrum generated by the spectrum generator 190. The X-ray spectrometer 200 shown in FIG. 6 can be similarly operated.

The present invention embraces configurations (e.g., configurations identical in function, method, and results or identical in purpose and advantageous effects) which are substantially identical to the configurations described in the above embodiments. Furthermore, the invention embraces configurations which are similar to the configurations described in the above embodiments except that their nonessential portions have been replaced. Additionally, the invention embraces configurations which are identical in advantageous effects to, or which can achieve the same object as, the configurations described in the above embodiments. Further, the invention embraces configurations which are similar to the configurations described in the above embodiments except that a well-known technique is added.

Having thus described my invention with the detail and particularity required by the Patent Laws, what is desired protected by Letters Patent is set forth in the following claims.

The invention claimed is:
1. An X-ray spectrometer comprising:
an X-ray detector for detecting X-rays and outputting a staircase waveform having steps whose heights correspond to energy levels of the X-rays;
a first differential filter having a time constant and operative to convert the staircase waveform into a first pulsed signal having peaks whose heights correspond to the heights of the steps;
an event detection portion for making a decision as to whether the first pulsed signal has exceeded a threshold value;
a noise event detection portion for making a decision as to whether a period during which the first pulsed signal is in excess of the threshold value is shorter than a given time;
a second differential filter having a time constant longer than the time constant of the first differential filter and operative to convert the staircase waveform into a second pulsed signal having peaks whose heights correspond to the heights of the steps;
a maximum value detection portion which, if the first pulsed signal is judged to be in excess of the threshold value, starts to detect a maximum value of the second pulsed signal; and
a decision portion for making a decision as to whether information about the maximum value is output, based on the decision made by the noise event detection portion.

2. An X-ray spectrometer comprising:
an X-ray detector for detecting X-rays and outputting a staircase waveform having steps whose heights correspond to energy levels of the X-rays;
a first differential filter having a time constant and operative to convert the staircase waveform into a first pulsed signal having peaks whose heights correspond to the heights of the steps;
an event detection portion for making a decision as to whether the first pulsed signal has exceeded a first threshold value;
a noise event detection portion for making a decision as to whether said first pulsed signal is below a second threshold value;
a second differential filter having a time constant longer than the time constant of the first differential filter and operative to convert the staircase waveform into a second pulsed signal having peaks whose heights correspond to the heights of the steps;
a maximum value detection portion which, if the first pulsed signal is judged to be in excess of the first threshold value, starts to detect a maximum value of the second pulsed signal; and
a decision portion for making a decision as to whether information about the maximum value is output, based on the decision made by the noise event detection portion.

3. An X-ray spectrometer as set forth in claim 2,
wherein said peaks of the first pulsed signal appear on a positive side of a reference level;
wherein said first threshold value is set on the positive side; and
wherein said second threshold value is set on a negative side of the reference level.

4. A sample analyzer including an X-ray spectrometer as set forth in any one of claims 1 to 3.

* * * * *